(12) United States Patent
Segal

(10) Patent No.: US 6,701,477 B1
(45) Date of Patent: Mar. 2, 2004

(54) METHOD FOR IDENTIFYING THE CAUSE OF YIELD LOSS IN INTEGRATED CIRCUIT MANUFACTURE

(75) Inventor: Julie Segal, Palo Alto, CA (US)

(73) Assignee: Hueristics Physics Laboratories, San Jose, CA (US)

( * ) Notice: Subject to any disclaimer, the term of this patent is extended or adjusted under 35 U.S.C. 154(b) by 506 days.

(21) Appl. No.: 09/591,603

(22) Filed: Jun. 9, 2000

(51) Int. Cl.⁷ .............................................. G01R 31/28
(52) U.S. Cl. ..................................................... 714/732
(58) Field of Search ......................................... 714/732

(56) References Cited

U.S. PATENT DOCUMENTS

| | | | |
|---|---|---|---|
| 5,475,695 A | | 12/1995 | Caywood et al. ............. 371/27 |
| 5,497,381 A | * | 3/1996 | O'Donoghue et al. ....... 714/745 |
| 5,515,384 A | * | 5/1996 | Horton, III ................. 714/732 |
| 5,539,752 A | | 7/1996 | Berezin et al. ............. 371/22.1 |
| 5,777,901 A | | 7/1998 | Berezin et al. ............. 364/578 |
| 5,822,218 A | | 10/1998 | Moosa et al. ............... 364/488 |
| 5,982,920 A | * | 11/1999 | Tobin et al. ................ 382/145 |
| 5,991,699 A | * | 11/1999 | Kulkarni et al. .............. 702/83 |
| 6,408,219 B2 | * | 6/2002 | Lamey et al. ............... 700/110 |
| 6,507,800 B1 | * | 1/2003 | Sheu ........................ 702/117 |
| 6,507,933 B1 | * | 1/2003 | Kirsch et al. ................. 716/4 |
| 2001/0051836 A1 | * | 12/2001 | Lamey et al. ............... 700/110 |

OTHER PUBLICATIONS

S. Naik, F. Agricola, and W. Maly, "Failure analysis of high–density CMOS SRAM's," IEEE Design Test Comput., vol. 10, pp. 13 23, Jun. 1993.*

Yu, J.; Ferguson, F.J.; Maximum likelihood estimation for failure analysis [IC yield]; IEEE Transactions on Semiconductor Manufacturing; vol.: 11 Issue: 4, pp.: 681–691, Nov. 1998.*

Ferguson, E.J.; Jianlin Yu; Maximum likelihood estimation for yield analysis [IC manufacture]; Proceedings IEEE International Symposium on Defect and Fault Tolerance in VLSI Systems, Nov. 6–8, 1996; pp.: 149–157.*

Chin, H.; Danai, K.; Improved flagging for pattern classifying diagnostic systems; IEEE Transactions on Systems, Man and Cybernetics, vol.: 23 Issue: 4 , Jul./Aug. 1993 pp.: 1101–1107.*

Young–Jun Kwon; Walker, D.M.H.; Yield learning via functional test data; Proceedings International Test Conference, Oct. 21–25, 1995 pp.: 626–635.*

W. Maly et al., "Systematic Characterization of Physical Defects for Fault Analysis of MOS IC Cells", 1984 IEEE International Test Conference, pp. 390–399.

C. Stapper et al., "Integrated Circuit Yield Management and Yield Analysis: Development and Implementation", May 1995 IEEE Transactions on Semiconductor Manufacturing, vol. 8, No. 2, pp. 95–102.

H. Balachandran et al., "Correlation of Logical Failures to a Suspect Process Step", 1999 ITC International Test Conference, pp. 458–466.

(List continued on next page.)

Primary Examiner—Albert Decady
Assistant Examiner—Joseph D. Torres
(74) Attorney, Agent, or Firm—Sierra Patent Group, Ltd.

(57) ABSTRACT

A method for determining the integrated circuit manufacturing operations that are the principle contributors to defect limited test yield loss comprises extracting the electrical faults for the important range of defect sizes from the layout data base; determining the signatures of the electrical response of faulted circuits to the input test stimuli; determining the statistical frequency distribution of the signatures for a fixed ratio of defect densities on the several process layers; determining the frequency distribution of the signatures observed in testing a wafer or group of wafers; and adjusting the defect densities amongst the process layers to minimize the difference between the predicted and observed frequency distributions such that the adjusted defect distribution provides a measure of the relative contribution of the process layers to yield loss.

2 Claims, 8 Drawing Sheets

OTHER PUBLICATIONS

A. Jee et al., "Carafe: An Inductive Fault Analysis Tool for CMOS VLSI Circuits", Board of Studies in Computer Engineering, University of California, Santa Cruz.

D. Y. Lepejian et al., "An Automated Failure Analysis (AFA) Methodology for Repeated Structures", Semiconductor Diagnosis and Test Corp.

J. Segal et al., "Predicting Failing Bitmap Signatures for Memory Arrays with Critical Area Analysis", 1999 IEEE Advanced Semiconductor Manufacturing Conference.

C. H. Stapper et al., "Yield Model for Productivity Optimization of VLSI Memory Chips with Redundancy and Partially Good Product", May 1980, IBM J. Research and Development, vol. 24, No. 3, pp. 398–409.

D. Ciplickas et al., "Predictive Yield Modeling for Reconfigurable Memory Circuits", 1998 IEEE/SEMI Advanced Semiconductor Manufacturing Conference, pp. 1–6.

J. Segal et al., "Determining Redundancy Requirements for Memory Arrays with Critical Area Analysis", 1999 IEEE Workshop on Memory Technology, Design, and Testing.

T. Tsujide et al., "Automatic Memory Failure Analysis Using an Expert System in Conjunction with a Memory Tester/Analyzer", 1993 IEEE/IRPS, pp. 184–189.

* cited by examiner

METHOD FOR IDENTIFYING THE CAUSE OF YIELD LOSS IN INTEGRATED CIRCUIT MANUFACTURE

BACKGROUND OF THE INVENTION

1. Field of the Invention

The present invention relates to the testing of integrated circuits. More particularly, the present invention relates to identifying the cause of yield loss in the integrated circuit manufacturing process.

2. The Prior Art

Integrated circuits have become the dominant form for the expression of electronic functions because of their ability to provide extensive functionality at moderate cost. Basic to the cost structure of modern integrated circuit (IC) technology is achieving high yields in the manufacturing process. A dominant yield-limiting factor, especially for digital circuits, is random fabrication defects.

Methods for identifying regions in which defects can cause failure-inducing faults, sometimes referred to as critical areas, from IC layouts are well known to those in the IC testing art. Such methods are discussed in Maly et al, "Systematic Characterization of Physical Defects for Fault Analysis of MOS IC Cells", 1984 IEEE International Test Conference, pp.390–399; Ferguson et al, "A CMOS Fault Extractor for Inductive Fault Analysis", IEEE Trans. on CAD, vol. 7, No. 11 Nov. 1988, pp. 1181–94; A. Jee and F. J. Ferguson, "Carafe: An Inductive Fault Analysis Tool for CMOS VLSI Circuits", Proceedings of the 11th VLSI Test Symposium, 1993, pp. 92–8; and Charles H. Stapper and Raymond J. Rosner, "Integrated Circuit Yield Management and Yield Analysis: Development and Implementation", IEEE Trans. on Semiconductor Manufacturing, Vol. 8, pp. 95–102 (1995).

There have also been efforts to predict the yield of integrated circuits. See, for example, U.S. Pat. No. 3,751,647 to Maeder et al., "Semiconductor and Integrated Circuit Device Yield Modeling"; U.S. Pat. No. 5,777,901 to Berezin et al. "Method and System for Automated Die Yield Prediction in Semiconductor Manufacturing"; U.S. Pat. No. 5,777,901 to Moosa et al., "Systems, Methods, and Computer Program Products for Prediction of Defect-Related Failures in Integrated Circuits".

Finally, there have been efforts at diagnosing the causes of the failures of individual ICs from electrical test results. See, for example, U.S. Pat. No. 5,475,695 to Caywood et al, "Automatic Failure Analysis System"; U.S. Pat. No. 5,808,919 to Priest et al., "Diagnostic System"; T. Tsujide et al, "Automatic Memory Failure Analysis Using an Expert System in Conjunction with a Memory Tester/Analyzer", International Reliability Physics Symp. PP. 184–9 (1993); D. Y. Lepejian, et al, "An Automated Failure Analysis (AFA) Methodology for Repeated Structures", 12th IEEE VLSI Test Symp. (1994); and Hari Balachandran, et al, "Correlation of Logical Failures to a Suspect Process Step", Proc. Int'l Test Conf. pp. 458–66 (1999).

In practice, the defect related faults in an IC manufacturing area occur in a dynamic manner, that is, the leading causes of failure fluctuate over time requiring that the failures must be continually monitored in order to know where defect reduction efforts should be focused to gain the greatest return. This requires an indicator that can quickly and continuously monitor the IC yield in order to direct the efforts appropriately. It is desirable that this indicator not increase the test time because the cost of testing ICs is often a significant contribution to the overall manufacturing cost.

Another characteristic of recent IC products is that their production lifetimes are decreasing. This means that yield enhancement information on a new product must be made available to a factory increasingly quickly.

It is an objective of this invention to use the statistical distribution of the electrical characteristics of failing parts, which will be referred to herein as a "signature", to predict the distribution of the processes that cause the failures. Using this information, the yield enhancement efforts can be focussed on the process steps for which improvements will provide the largest increase in yield.

It is a further objective of this invention to provide a method of quickly developing the correlations between physical layout and electrical failures needed to apply statistical failure distribution results to identification of the fault-causing defect distribution.

BRIEF DESCRIPTION OF THE INVENTION

According to the present invention, a method is disclosed for utilizing information extracted from the physical design of an integrated circuit, usually referred to as the chip layout, in combination with the results of electrical tests of completed integrated circuits, to determine the relative fraction of failures caused by each layer in the IC manufacturing.

This can be divided into two operations: that of extracting information from the IC design and test program and operating on the information to put it in a form that it is useful for the defect origin prediction and that of applying the extracted knowledge to the results of test operations to identify the probability of the various layers causing the observed failures. The first operation must be performed only once per design/test set combination. The second operation may be performed repeatedly, e.g., once for each lot of ICs tested. Each operation will be discussed in turn.

The knowledge extraction operation begins by analyzing the chip layout layer by layer to identifying the regions in which a defect can cause a fault, i.e. an alteration of the circuit topology, and the relative likelihood that each fault will occur for a defect of a given size. (Each layer may be thought of as a conducting layer that may be incorrectly linked to another conductor to form a bridge fault or may be incorrectly broken to form a break fault.)

Once the faults are identified, the electrical output responses to a set of input stimuli are found. The set of responses to each fault is called a signature. In general, several faults may have the same signature. The fraction of the faults that respond with a unique signature to a set of input stimuli may be taken as a measure of the suitability of a stimuli set for diagnosis.

The relative signature distribution is obtained for each process layer. If there are i signatures and j process layers, the result can be represented as an i by j matrix. This matrix represents the knowledge base.

When a wafer or batch of wafers is tested with the stimuli, the results for the failing ICs may be arranged a distribution of signatures. This measured distribution must be composed of a linear combination of the signature distributions for the process layers where the distribution for each layer is weighted by the relative contribution of that layer to the failures observed. The measured signatures distribution can be inverted with help of the knowledge base matrix to yield the relative contribution of each process layer to the failures observed.

BRIEF DESCRIPTIONS OF THE DRAWING FIGURES

DETAILED DESCRIPTION OF THE INVENTION

Persons of ordinary skill in the art will realize that the following description of the present invention is illustrative only and not in any way limiting. Other embodiments of the invention will readily suggest themselves to such skilled persons having the benefit of this disclosure.

A method for determining the integrated circuit manufacturing operations that are the principle contributors to defect limited test yield loss comprises extracting the electrical faults for the important range of defect sizes from the layout data base; determining the signatures of the electrical response of faulted circuits to the input test stimuli; determining the statistical frequency distribution of the signatures for a fixed ratio of defect densities on the several process layers; determining the frequency distribution of the signatures observed in testing a wafer or group of wafers; and adjusting the defect densities amongst the process layers to minimize the difference between the predicted and observed frequency distributions such that the adjusted defect distribution provides a measure of the relative contribution of the process layers to yield loss.

Figure 1:
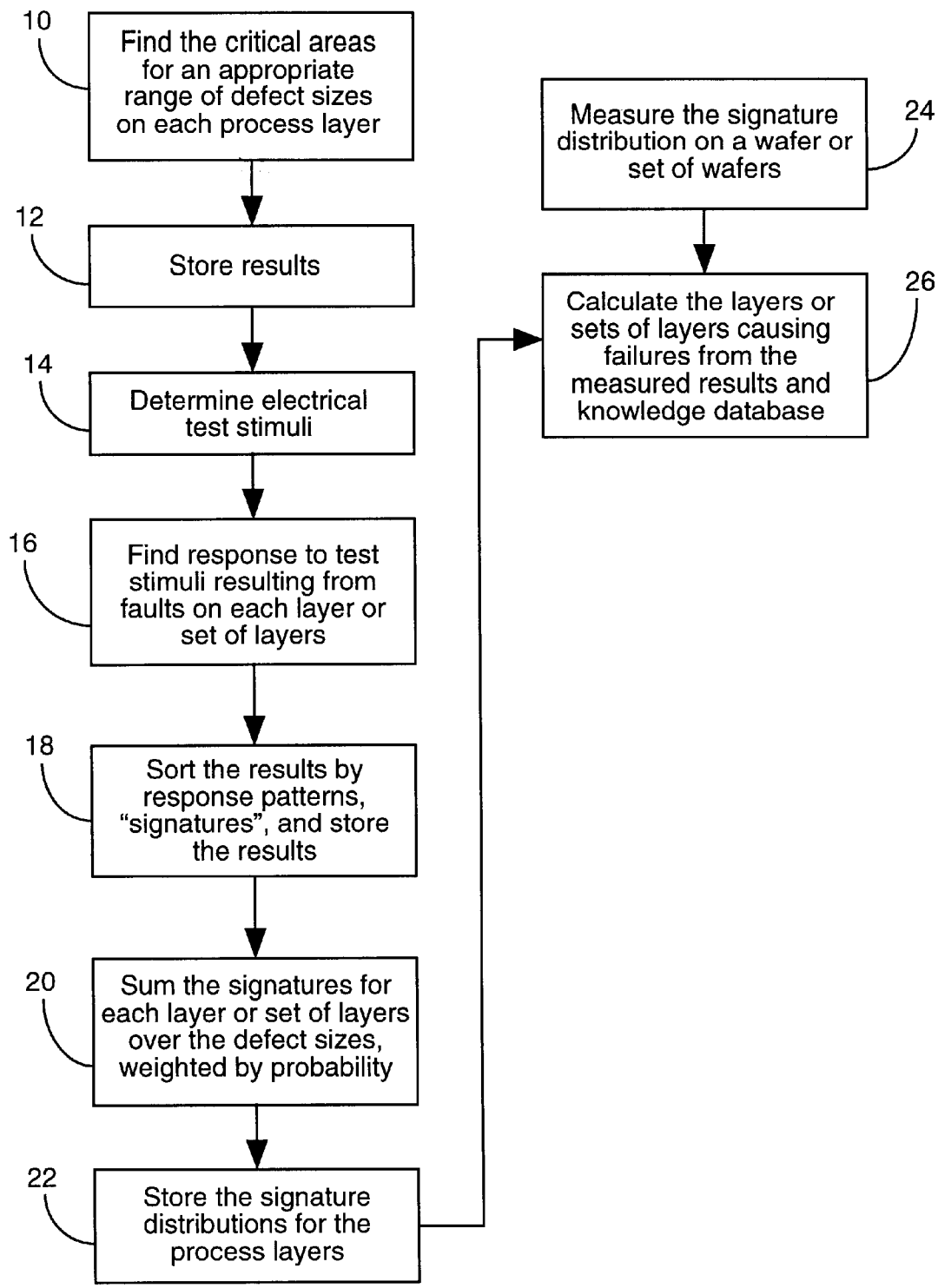
FIG. 1 is a flow chart for the overall method of determining failure cause by process layer.

FIG. 1 is a flow chart illustrating one method according to the present invention. The actions depicted in the blocks 10, 12, 14, 16, 18, and 22 in FIG. 1 represent the knowledge acquisition phase of this invention. The actions in the blocks 24 and 26 in FIG. 1 represent the knowledge application phase of this embodiment of the present invention.

The first thing that must be done is to determine where and with what probability defects of differing sizes can cause faults to occur on or between process layers. This is accomplished at block 10 of FIG. 1.

Clearly not all defects can cause defects at all locations. It should be clear that defects smaller than the minimum feature size cannot lead to bridging faults because they are too small to bridge adjacent lines that have even the minimum spacing. Such defects are also too small to cause breaks in a line because the cross section of the smallest line exceeds the defect size. It is also well known that the probability of defects occurring is proportional to 1-a where 1 is the defect size and a is a positive parameter that is found empirically to be about 3. This means that a defect that is 4 times the minimum feature size is 1/64 times as likely to occur as a defect of the minimum feature size. The range of defects size between the minimum feature size and about 4 times the minimum feature size is referred to as the fault-causing range of defects because most faults are caused by defects in this size range.

Figure 2:
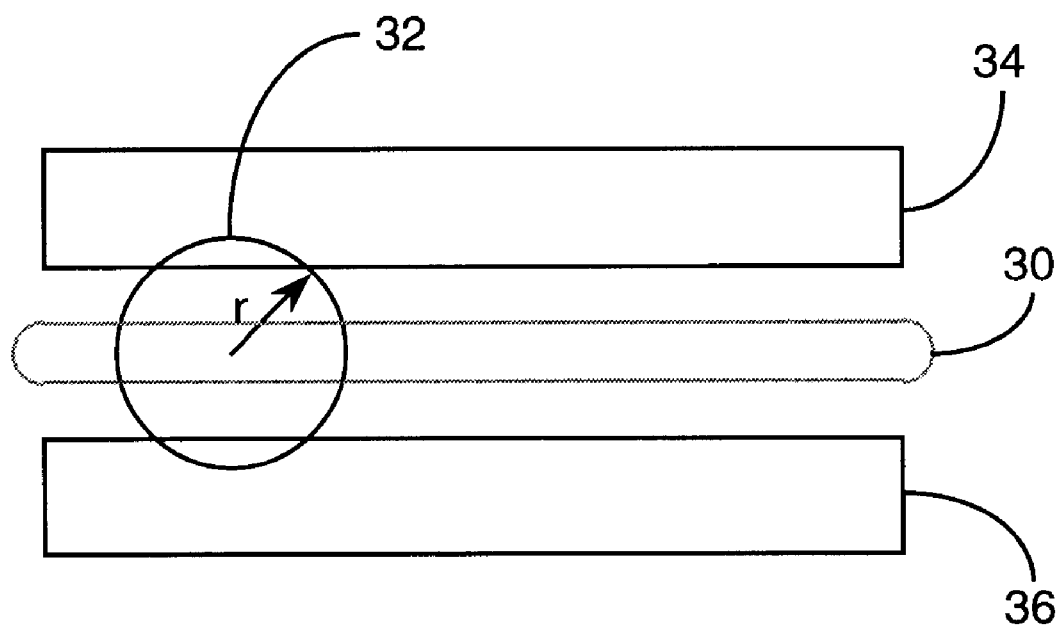
FIG. 2 illustrates the concept of critical area.

For example, a bridging defect that is smaller than the minimum spacing between two traces on a layer can not bridge the two traces. If the bridging defect is larger than the minimum spacing between the two traces, it may cause a fault, depending on where the defect is located. As is illustrated in FIG. 2, there is a locus of points 30 at which the center of a circular defect 32 of radius r can lie in order to bridge two conducting traces 34 and 36. This locus of points 30 is called the critical area. Although illustrated here for an idealized circular defect, persons of ordinary skill in the art this concept can be generalized. The probability that a defect will cause a fault is proportional to the critical area of the defect for that fault. Thus, calculation of the critical areas for the various possible faults provides a relative measure of the fault probabilities. Those of ordinary skill in the art are well aware of several methods of computing the critical areas of a given layout for defects of a selected size. Methods for extracting critical areas are well known in the art and are discussed in, for example, Maly et al, "Systematic Characterization of Physical Defects for Fault Analysis of MOS IC Cells", 1984 IEEE International Test Conference, pp. 390–399; Ferguson et al, "A CMOS Fault Extractor for Inductive Fault Analysis", IEEE Trans. on CAD, vol. 7, No. 11 Nov. 1988, pp. 1181–94; A. Jee and F. J. Ferguson, "Carafe: An Inductive Fault Analysis Tool for CMOS VLSI Circuits", Proceedings of the 11th VLSI Test Symposium, 1993, pp. 92–8.

Once the critical areas are determined for each layer as a function of defect size, these results are stored at block 12.

Next, at block 14, the electrical test stimuli to be used are applied to the IC under test. The signatures depend on the electrical tests that are employed which are, in turn, dependent upon the type of IC being tested. If the IC were a logic part, the test would consist of a series of test vectors (i.e. a series of input logic patterns) and the output of the IC would be a series of output vectors (i.e. another series of logic patterns). In the case that the IC is a memory, the test usually consists of writing and reading a number of data patterns to and from the IC under test. This is often done at several different supply voltages and possibly at more than one temperature. While the test methodology varies with the device to be tested, this is a subject that has been studied extensively for all commercially imported circuit types and is very well known to persons of ordinary skill in the art.

The signatures depend on the electrical tests that are employed which are, in turn, dependent upon the type of IC being tested. If the IC were a logic part, the test would consist of a series of test vectors (i.e. a series of input logic patterns) and the output of the IC would be a series of output vectors (i.e. another series of logic patterns). In the case where the IC is a memory, the test usually consists of writing and reading a number of data patterns to and from the IC under test. This is often done at several different supply voltages and possibly at more than one temperature.

For logic testing, the number of input and output vectors are generally the same, but the size of the vectors (i.e. the number of elements in the logic patterns) may not be the same. For this case the signatures might be as detailed as all of the output levels for all of the vectors, but more likely would be a compression of this information. The compressed. signature might be as simple as entering a "0" if the measured output vector matched the expected value and a "1" if it did not. The compression algorithm could also take a large number of other forms that would offer either more compression, more detail or both as will be apparent to one of ordinary skill in the art.

For memory testing, the signature could also be as detailed as the pass/fail pattern after reading each pattern. It is likely that the patterns would be compressed for the memory case also. For the example in this disclosure, it will be assumed that the signatures take the form of a geometrical description of the pattern of the failing bits summed over all of the tests, e.g. single bits, rows, columns, etc., but it will be apparent to one of ordinary skill in the art that there are a large number of other equivalent possibilities, all of which are intended to fall within the scope of the present invention.

At block 16, the responses to the electrical test stimuli are collected. Knowing the possible faults in the IC (or section of the IC) under test, and the electrical stimuli to be used in the test, the responses of the faulted ICs to the test vectors can be determined by one of several ways well known in the art. For example, the responses could be determined with a analog circuit simulator, such as the well-known SPICE simulator, or with a logic simulator, e.g. Verilog. This is discussed, for example, in D. Y. Lepejian, et al, "An Automated Failure Analysis (AFA) Methodology for Repeated Structures", 12th IEEE VLSI Test Symp. (1994). They can also be determined with a heuristic algorithm as will be described later. The signatures are found for the faults on each layer or set of layers individually for a range of defect sizes. A range of defect sizes is a fixed ratio of defect densities on each process layer. The defect density being the amount of defects in a layer. The defect sizes are chosen to match those expected to be important for the process technology used for the IC to be tested. For example, bridging defects less than the minimum feature spacing can be ignored, and it is known that the probability of a defect decreases rapidly with defect size. It has been often found that the number of defects is proportional to (size)$^{-3}$. For defect size distributions like this, defect sizes ranging from about the minimum feature size to about four times the minimum feature size capture most of the important features.

Once the critical area associated with each fault has been found, and the signatures from the faults found, the statistical frequency distribution of the signatures can be found for each layer. These responses are sorted so that the critical areas of all faults on a given process layer with the same signature are combined and stored as those of a common failure signature. This is illustrated at block 18.

Figure 3:
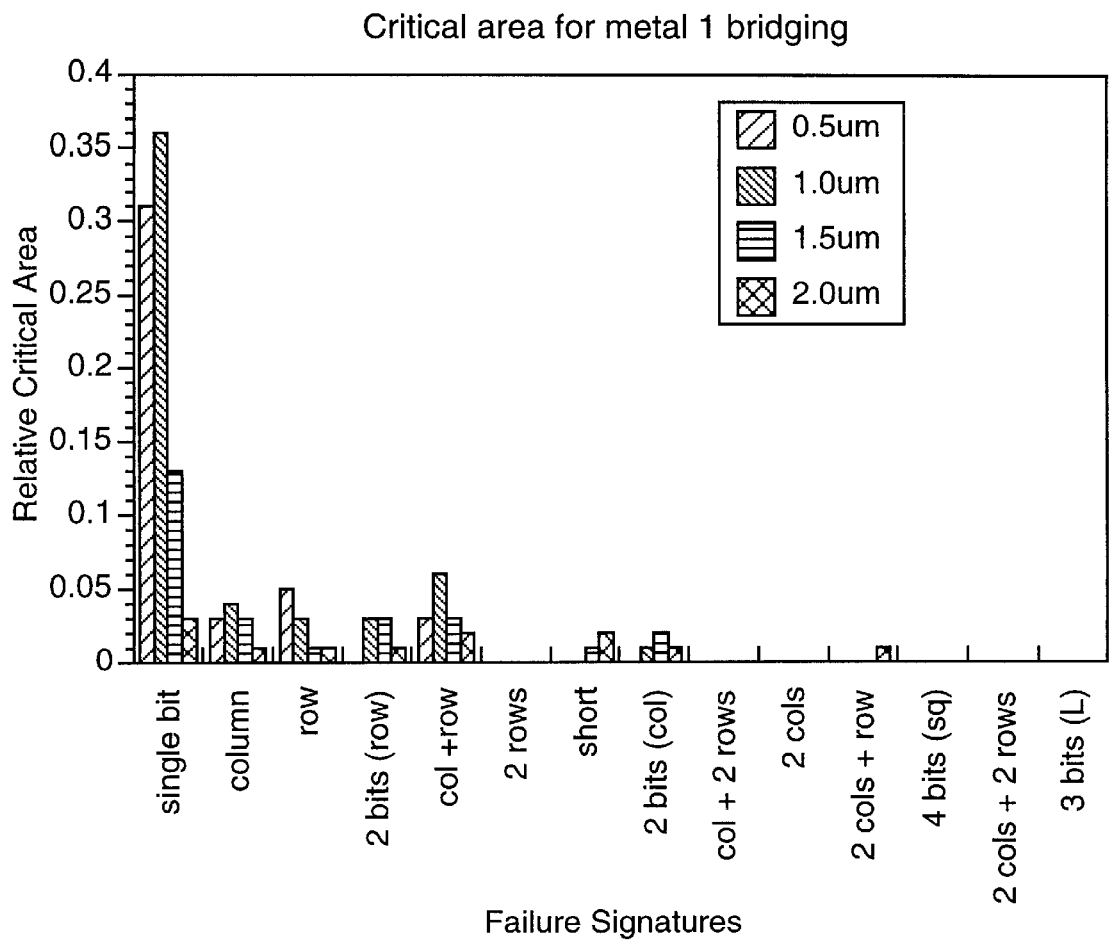
FIG. 3 shows an example of a signature distribution for a process layer for the case of a memory array.

The signatures are found for the faults on each layer or set of layers individually for a range of defect sizes. The defect sizes are chosen to match those expected to be important for the process technology used for the IC to be tested. For example, bridging defects less than the minimum feature spacing can be ignored, and it is known that the probability of a defect decreases rapidly with defect size. It has been often found that the number of defects is proportional to (size)$^{-3}$. See, for example, Charles H. Stapper and Raymond J. Rosner, "Integrated Circuit Yield Management and Yield Analysis: Development and Implementation", IEEE Trans. on Semiconductor Manufacturing, Vol. 8, pp. 95–102 (1995). For defect size distributions like this, defect sizes ranging from about the minimum feature size to about four times the minimum feature size capture most of the important features. The critical areas for the different defect sizes are multiplied by a factor proportional to the probability of defects of that size occurring and then the signatures are summed over defect sizes for each process layer or set of process layers to yield the signature distribution for each layer. This is illustrated at block 20. An example distribution for a memory IC for the metal 1 layer is shown in FIG. 3.

Mathematically speaking, there are m signatures into which the failing devices are classified. Examples of signatures for a memory are single bits, paired bits, rows, columns, etc. Each set of signatures should contain the signature noa for "not any other".

There are n layers, or layer combinations, that can cause a fault. Examples of single-layer faults are metal-1 breaks or poly bridges. Examples of two-layer faults are metal-1-to-poly shorts or poly-to-active shorts through the gate oxide.

All faults on a given layer fall into one of the signatures. Thus, the total number of faults on the i$^{th}$ level can be described by the equation $$f_i = \sum_{j=1}^{m} a_{i,j} \qquad \text{(eq. 1)}$$

where $a_{ij}$ is the number of faults on the i$^{th}$ layer that exhibit failure signature j. The actual number of faults that occur depends on the absolute defect density, but the relative number of faults on each layer, defined by $$a^*_{i,j} = a_{ij}/f_i,$$

can be extracted from the relative critical areas and an analysis of the results of each fault. With this definition, it is clear that $$1 = \sum_{j=1}^{m} a^*_{i,j}. \qquad \text{(eq. 2)}$$

Figure 4:
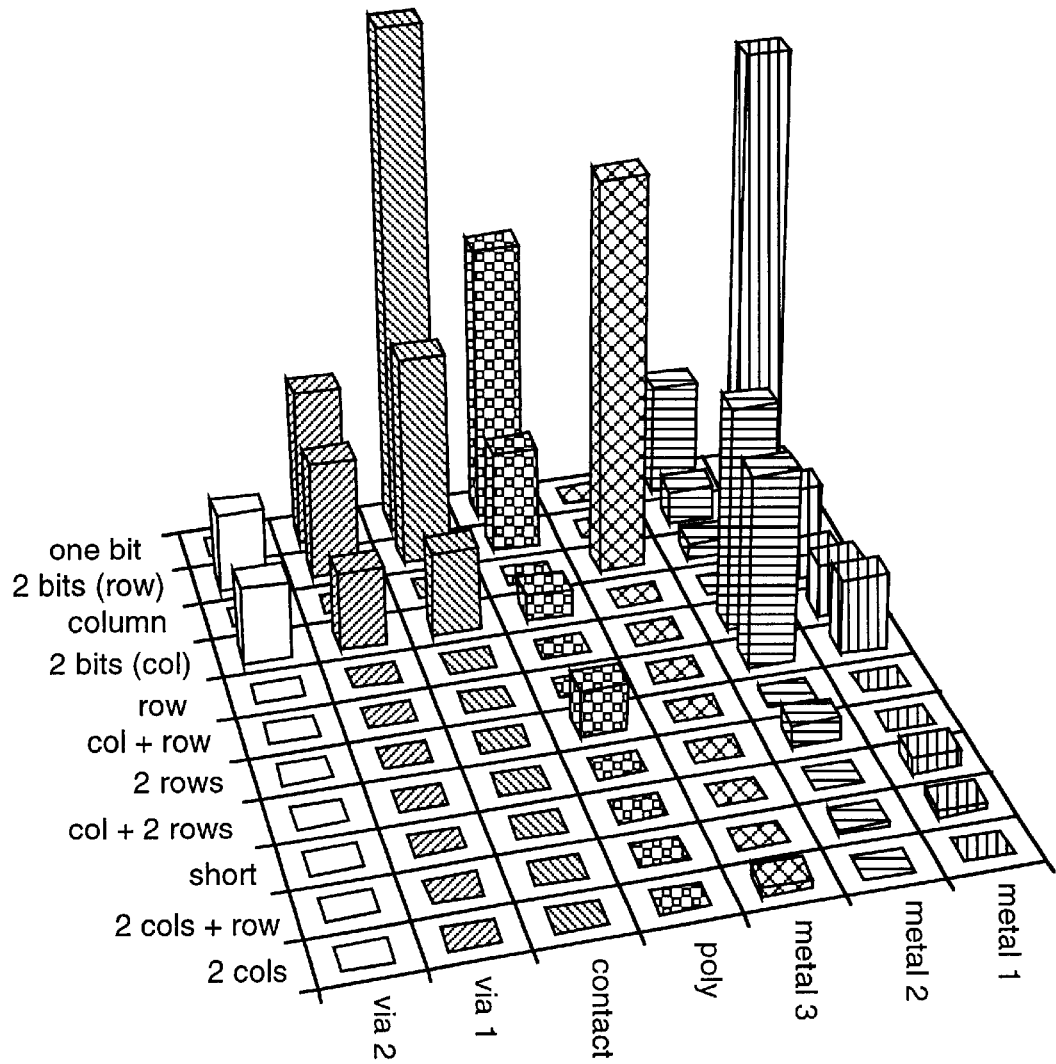
FIG. 4 shows relative signature frequencies associated with different process layers.

The elements $a^*_{i,j}$ are represented graphically in FIG. 4. Extraction of the information contained in the matrix with elements $a^*_{i,j}$ in eq. 2 completes the knowledge extraction phase of the method of this invention. This information is stored at block 22 for application to the test results.

After the test stimuli are applied to a wafer or set of wafers, the failing ICs are classified as to their failure signatures by measuring the signature distribution on the wafer or set of wafers at block 24. The number of wafers in the test lot should be large enough that the number of signatures classified is large enough to be statistically significant. As is well known to those of ordinary skill in the art, there are well establish tests for statistical significance.

If the probability of a fault being caused by a fault were the same for the faults on all layers or sets of layers, the relative distribution of the faults would be just that found by summing the relative probability of each fault signature over all of the process layers.

Figure 5:
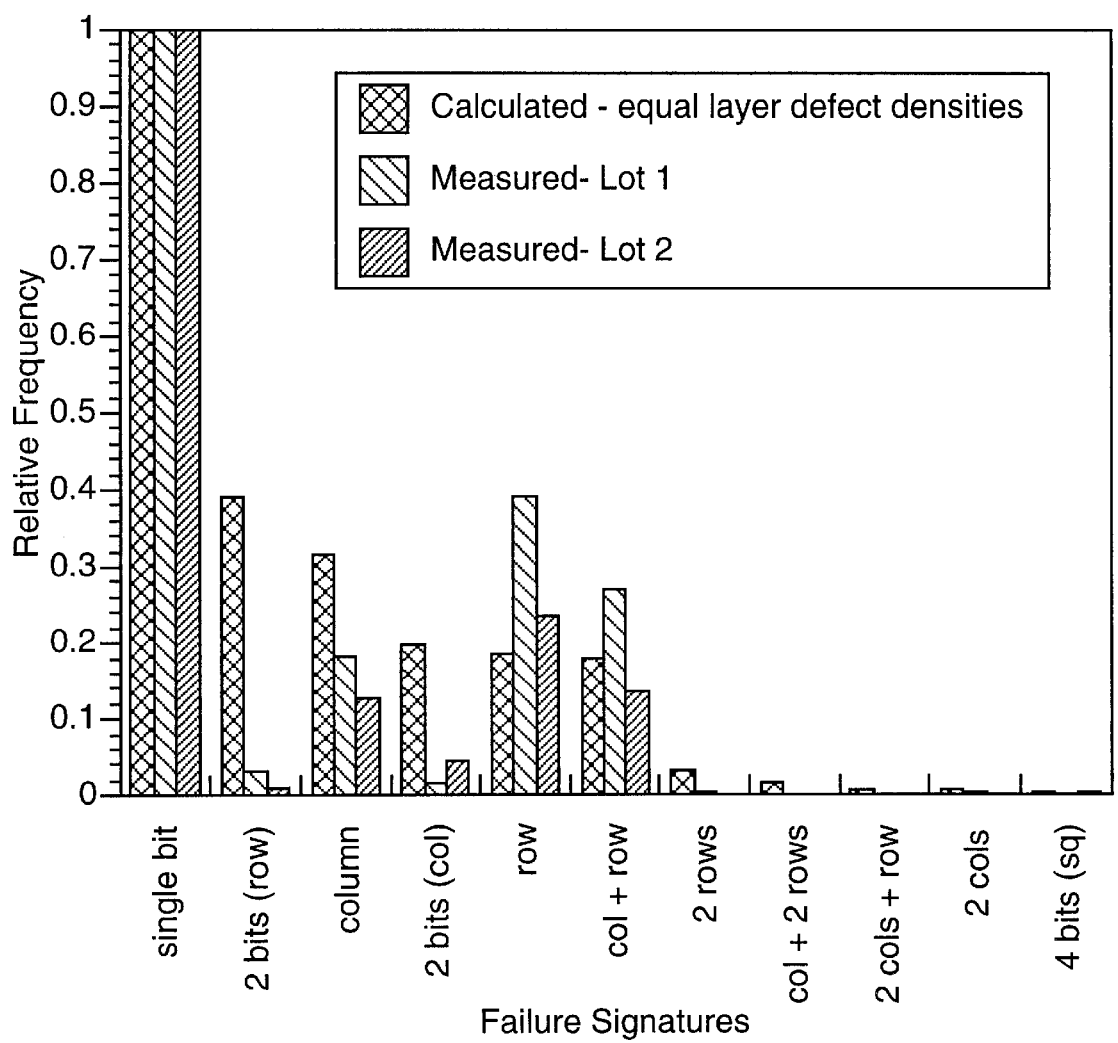
FIG. 5 shows the signature distribution that would result from equal density of defects on all process layers and the measured signature distributions from two lots of memory ICs.
Figure 6:
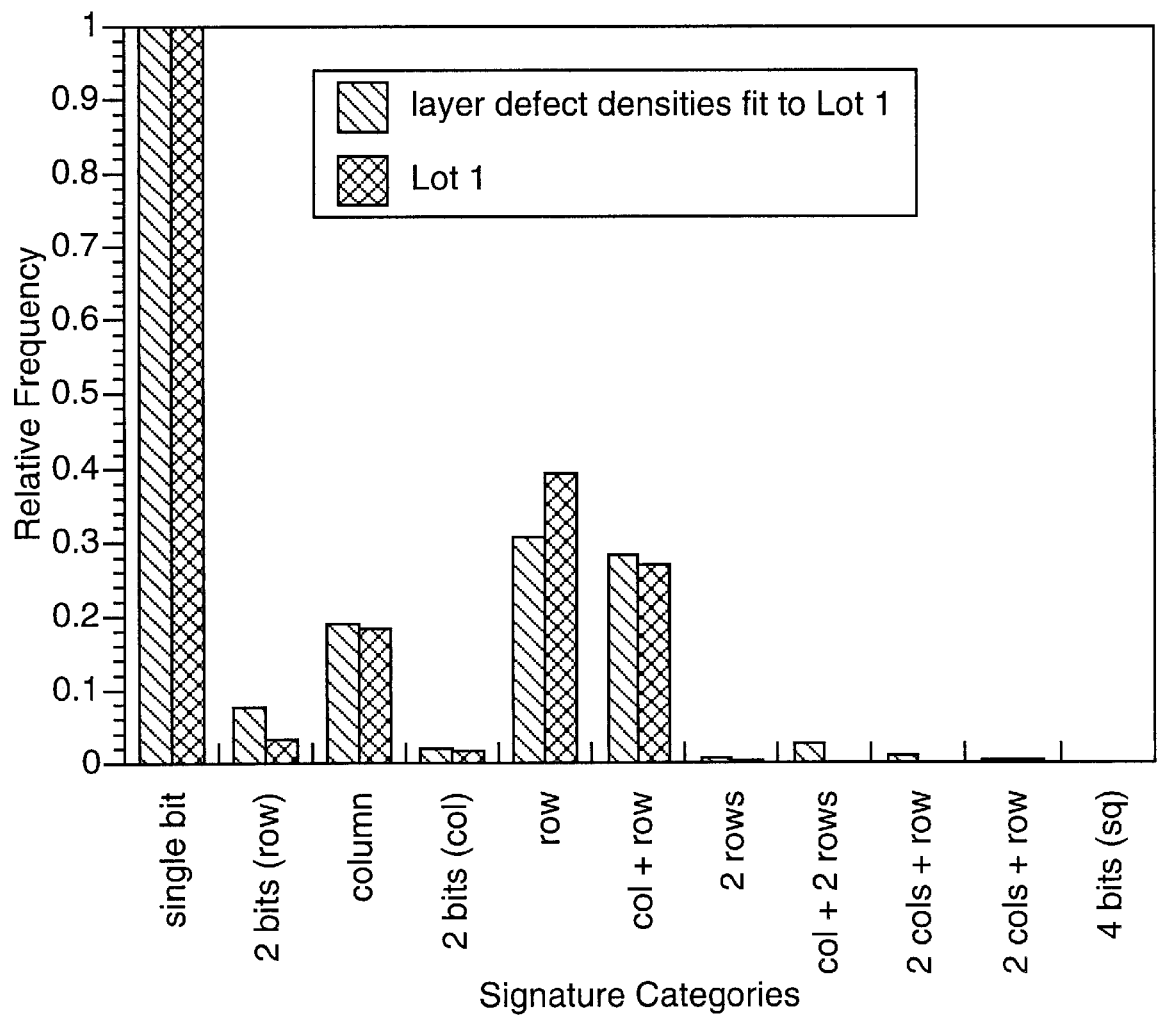
FIG. 6 shows the results of adjusting the defect densities on different process layers to match the measured results from lot 1.
Figure 7:
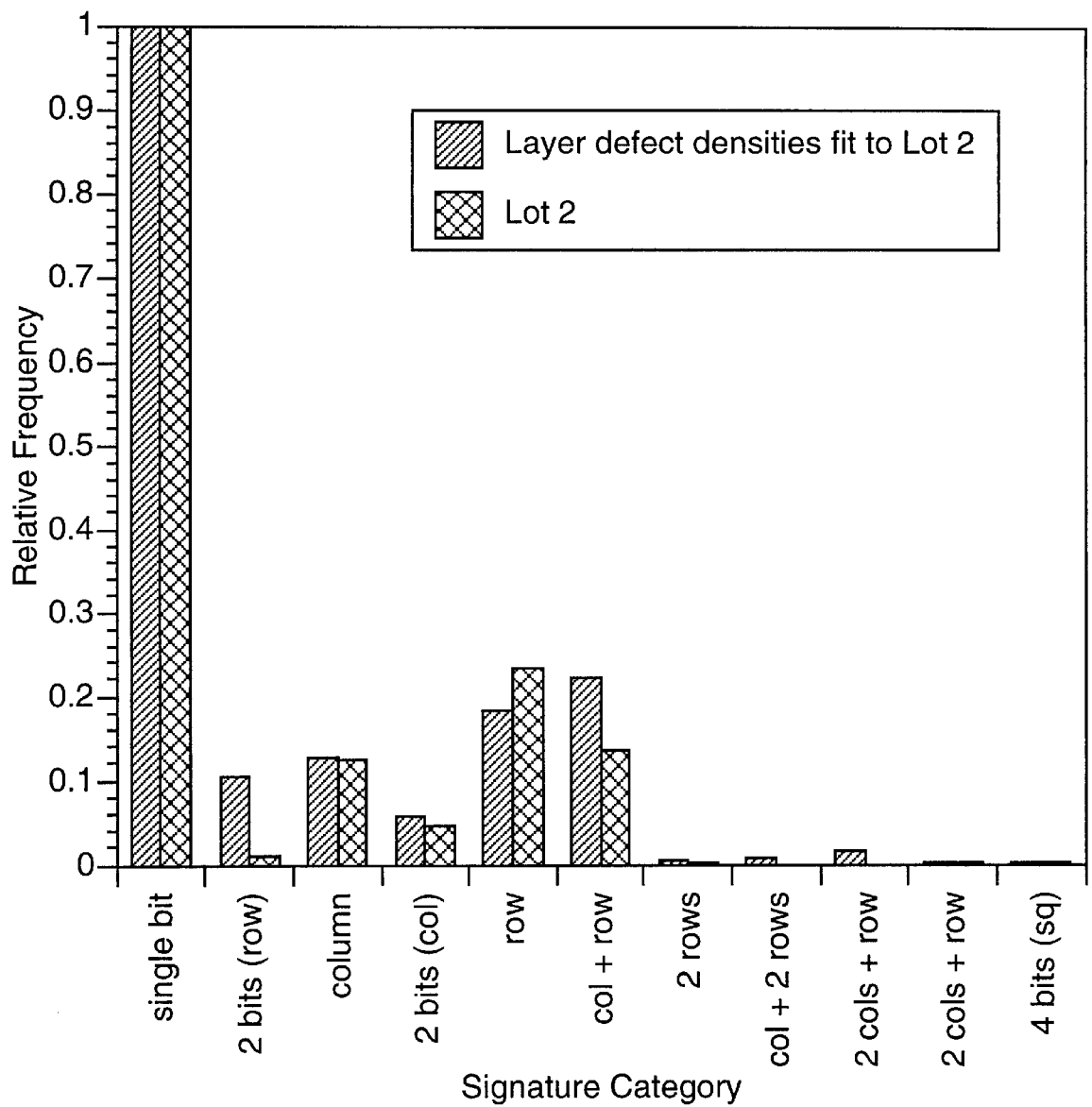
FIG. 7 shows the results of adjusting the defect densities on different process layers to match the measured results from lot 2.

This result is shown is FIG. 5 for an SRAM design and compared with data on the failing signature distribution of two fabrication lots of that design. Clearly, the relative distributions measured on the two fabrication lots are not that calculated with the assumption of equal likelihood of faults on any layer. However, if the relative probabilities of faults on the various layers are allowed to be unequal, the measured and calculated distributions can be bought into reasonable agreement as is illustrated in FIGS. 6 and 7.

These observations can be expressed mathematically by noting that failures can be classified by signatures such that the total number of failures, F, is given by $$F = \sum_{j=1}^{m} b_j \quad \text{(eq. 3)}$$

where $b_j$ is the number of failures occurring with signature j. The relative occurrence of observed failure signatures, $b^*_j$, can be defined by $$1 = \sum_{j=1}^{m} b_j/F = \sum_{j=1}^{m} b^*_j. \quad \text{(eq. 4)}$$

The about shows the ratio theoretical failures compared to the observed failures. However, since each observed failure must be the result of a fault on one of the i layers, $$F = \sum_{i=1}^{n} c_i. \quad \text{(eq. 5)}$$

The relative occurrence of faults on the i layers, $c^*_i$, can be defined by $$1 = \sum_{i=1}^{n} c_i/F = \sum_{i=1}^{n} c^*_i. \quad \text{(eq. 6)}$$

The about shows the ratio theoretical failures compared to the observed failures. The relative occurrence of a signature $b^*_j$ is given by the product of the fraction of the faults occurring on the $i^{th}$ layer by the fraction of the failures caused by faults on layer i that have signature type j, i.e., $$b^*_j = \sum_{i=1}^{n} a^*_{i,j} \cdot c^*_i. \quad \text{(eq. 7)}$$

Summing over all of the observed failures yields $$\sum_{j=1}^{m} b^*_j = \sum_{j=1}^{m} \sum_{i=1}^{n} a^*_{i,j} \cdot c^*_i. \quad \text{(eq. 8)}$$

In matrix notation, eq. 8 may be written as $$\begin{bmatrix} b^*_1 \\ \ldots \\ b^*_n \end{bmatrix} = \begin{bmatrix} a^*_{1,1} & \ldots & a^*_{1,n} \\ \ldots & \ldots & \ldots \\ a^*_{m,1} & \ldots & a^*_{m,n} \end{bmatrix} \begin{bmatrix} c^*_1 & \ldots & c^*_m \end{bmatrix} \quad \text{(eq. 9)}$$

which has the formal solution $$[c^*_1 \ \ldots \ c^*_m] = \begin{bmatrix} a^*_{1,1} & \ldots & a^*_{1,n} \\ \ldots & \ldots & \ldots \\ a^*_{m,1} & \ldots & a^*_{m,n} \end{bmatrix} \begin{bmatrix} b^*_1 \\ \ldots \\ b^*_n \end{bmatrix} \quad \text{(eq. 10)}$$

There are a number of well known methods for the evaluation of eq. 10. The important thing is that the fraction of failures resulting from each layer is determined solely by an observed set of values, $b^*_1$, and a set of values, $a^*_{i,j}$, that can be extracted from the layout for a set of test stimuli. This is illustrated at block 26.

As mentioned above, the response of the faulted parts to the input stimuli may be found by one of several well-known simulation techniques. However, experience has shown that this may be computationally intensive and consequently take both considerable time and resources for many cases of practical interest.

A heuristic approach has been developed according to the present invention for the commercially important case of memory arrays that allows the signatures to be obtained in several orders of magnitude less time and resources than with analog circuit simulation. This approach sacrifices the ability to discriminate the behavior of some defects that experience has shown to be less important (such as bridges between diffusion regions in the substrate) for the ability to very quickly obtain signatures so that practical yield enhancement work can begin. This approach does include the implicit assumption that the test patterns applied to the device provide coverage of all important faults.

Figure 8:
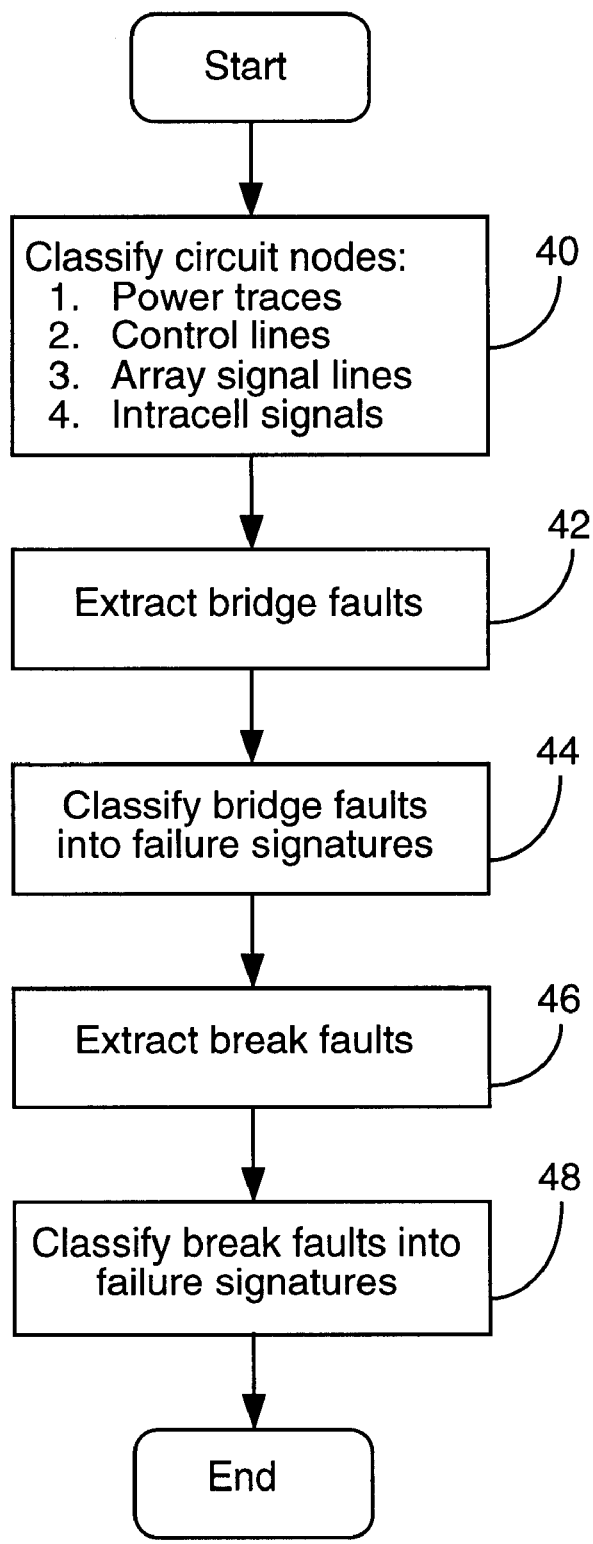
FIG. 8 is a flow chart of a method according to the present invention for quickly finding the signatures for a given set of defects.

This approach will be described with reference to FIG. 8. According to this embodiment of the present invention, the internal circuit nodes are classified in block 40 as being either power lines, e.g. VSS or VDD, control lines driven by the peripheral circuitry external to the memory core, e.g. word lines, array signal lines, bit lines, and intra-cell signals, such as the cross coupled signals for the latch in an SRAM cell. It is generally true that the bit lines act, in different operating modes, as both control lines or signal lines, but they are classified as signal lines. The electrical nodes can be automatically identified with the assistance of layout-vs-schematic software, if necessary. However, it is usually the case that a memory array can be analyzed in terms of a small repeating block of, typically, 3×3, 3×4 or 4×4 cells. For such small arrays, the various lines can be identified manually.

Next the bridge faults are extracted by any one of several methods well known to those of ordinary skill in the art as shown in Block 42.

The bridge fault failures are classified in accordance with the following rules:
1. Power traces to power traces at different bias: short
2. Power trace to any other node: non-power node fails
3. Control or array signal line to another such line: both lines fail.
4. Control line to intra-cell node: affected cell fails.
5. Array signal line to memory cell: signal line and cell both fail.
6. Intra-cell signals: only affected cells fail.

Once the failures are classified according to the above rules, the signatures are easily determined at block 44 by the topology of the failing elements.

After the bridging faults signatures are determined, the break faults are extracted by any one of several methods well known to those of ordinary skill in the art at block 46.

The break fault failures are classified at Block 48 in accordance with the following rules:
1. Control or signal line broken: all cells on the line that don't lie between the fault and the peripheral circuit to which the line is connected fail.
2. Intra-cell signals: only affected cells fail.
3. Connection between any array line, power, control, or signal, and cell: only cell fails.
4. Power trace: all cells past the break in the direction away from the power supply fail, e.g. if a row is supplied with VDD from the right side of the array, all cells on the row to the left of the break fail.

Again, once the failures are classified according to the above rules, the signatures are easily determined by the topology of the failing elements. Thus, both bridge and break signatures are determined. After these determinations, the defect densities among the process layers are adjusted to minimize the difference between the statistical frequency distribution of the signatures and the observed frequency distributions of the signatures. The adjusted defect distribution provides a measure of the relative contribution of each process layer to yield loss of wafer(s).

While embodiments and applications of this invention have been shown and described, it would be apparent to those skilled in the art that many more modifications than mentioned above are possible without departing from the inventive concepts herein. The invention, therefore, is not to be restricted except in the spirit of the appended claims.

What is claimed is:

1. A method for determining the integrated circuit manufacturing operations that are the principle contributors to defect limited test yield loss comprising:

extracting electrical faults for a fault-causing range of defect sizes from a layout database;

determining signatures of the electrical response of faulted circuits to input test stimuli wherein the signatures comprises topological patterns of failing bits observed on memory array;

determining a statistical frequency distribution of the signatures for a fixed ratio of defect densities on each process layer;

determining an observed frequency distribution of the signatures observed in testing a wafer or group of wafers; and adjusting defect densities amongst the process layers to minimize the difference between the statistical frequency distribution and the observed frequency distribution such that the adjusted defect densities provide a measure of the relative contribution of the process layers to yield loss.

2. A method for determining the integrated circuit manufacturing operations that are the principle contributors to defect limited test yield loss comprising:

classifying each circuit node as one of a plurality of classes;

extracting electrical bridge faults from the layout;

classifying each of said extracted bridge faults into failure signatures database wherein classifying said extracted bridge faults comprises classifying each of said bridge faults as at least one of a class selected from a group of classes consisting of power traces to power traces at different bias, short, power trace to any other node, non-power node fails, control or array signal line to another such line, both lines fail, control line to intra-cell node: affected cell fails, array signal line to memory cell, signal line and cell both fail, intra-cell signals, and only affected cells fail;

extracting electrical break faults from the layout database; and classifying each of said extracted break faults into failure signatures, wherein classifying said extracted bridge faults comprises classifying said break faults as at least one of a class selected from a group of classes consisting of control line broken, signal line broken, all cells on a line that do not lie between the fault and the peripheral circuit to which the line is connected fail, intra-cell signals, only affected cells fail, connection between any array line, power, control, or signal, and cell, only cell fails; power trace, and all cells past the break in the direction away from the power supply fail.

* * * * *